(12) United States Patent
Rezachek

(10) Patent No.: US 8,584,508 B2
(45) Date of Patent: Nov. 19, 2013

(54) PHOTOACOUSTIC SENSOR WITH ADAPTIVE OPERATING FREQUENCY

(75) Inventor: Thomas M. Rezachek, Cottage Grove, MN (US)

(73) Assignee: Honeywell International Inc., Morristown, NJ (US)

( * ) Notice: Subject to any disclaimer, the term of this patent is extended or adjusted under 35 U.S.C. 154(b) by 51 days.

(21) Appl. No.: 13/431,724

(22) Filed: Mar. 27, 2012

(65) Prior Publication Data

US 2012/0272719 A1    Nov. 1, 2012

Related U.S. Application Data

(60) Provisional application No. 61/479,221, filed on Apr. 26, 2011.

(51) Int. Cl.
*G01N 22/00* (2006.01)
*G01N 21/00* (2006.01)

(52) U.S. Cl.
USPC .......................................... 73/24.02; 356/437

(58) Field of Classification Search
USPC .......... 73/24.02; 356/437–439, 928, 931, 932
See application file for complete search history.

(56) References Cited

U.S. PATENT DOCUMENTS

| | | | |
|---|---|---|---|
| 4,200,399 A | 4/1980 | Kimble | |
| 5,780,724 A | 7/1998 | Olender et al. | |
| 6,552,792 B1 * | 4/2003 | Pilgrim et al. | 356/432 |
| 6,608,683 B1 * | 8/2003 | Pilgrim et al. | 356/432 |
| 6,618,148 B1 | 9/2003 | Pilgrim et al. | |
| 7,644,606 B2 * | 1/2010 | Sheen et al. | 73/24.02 |
| 2008/0127715 A1 | 6/2008 | Kosterev | |
| 2008/0180675 A1 * | 7/2008 | Sheen et al. | 356/437 |
| 2009/0266144 A1 | 10/2009 | Rezachek | |
| 2010/0011836 A1 | 1/2010 | Kalkman et al. | |
| 2010/0147051 A1 | 6/2010 | Tobias | |

FOREIGN PATENT DOCUMENTS

DE    10112579 A1    10/2002

OTHER PUBLICATIONS

"European Application Serial No. 12165238.2, Office Action mailed Aug. 28, 2012", 6 pgs.
"European Application Serial No. 12165238.2, European Search Report mailed Aug. 13, 2012", 5 pgs.
"European Application Serial No. 12165238.2, Response filed Feb. 27, 2013 to Office Action mailed Aug. 28, 2012", 19 pgs.
Rossi, A., et al., "Optical enhancement of diode laser-photoacoustic trace gas detection by means of external Fabry-Perot cavity", *Applied Physics Letters*, 87, (2005), 041110-1-041110-3.

\* cited by examiner

*Primary Examiner* — Hezron E Williams
*Assistant Examiner* — Nathaniel Kolb
(74) *Attorney, Agent, or Firm* — Schwegman, Lundberg & Woessner, P.A.

(57) ABSTRACT

Some embodiments relate to a photoacoustic sensor that includes a gas cell having an opening and a detector to collect pressure fluctuations within the gas cell to determine a spectral content of the pressure fluctuations within the ambient environment. The photoacoustic sensor further includes a light source to generate radiation to radiate sample gas within the gas cell and a control that receives signals from the detector that represent the spectral content of the pressure fluctuations within the ambient environment. The control adjusts a frequency of the radiation produced by the light source to a frequency that conflicts less with the spectral content of the pressure fluctuations within the ambient environment. The detector generates output electrical signals in response to acoustic signals generated by pressure fluctuations of the radiated sample gas.

20 Claims, 3 Drawing Sheets

PHOTOACOUSTIC SENSOR WITH ADAPTIVE OPERATING FREQUENCY

RELATED APPLICATIONS

This application claims priority to U.S. Provisional Application Ser. No. 61/479,221 (entitled PHOTOACOUSTIC SENSOR WITH ADAPTIVE OPERATING FREQUENCY, filed Apr. 26, 2011), which application is incorporated herein by reference.

TECHNICAL FIELD

Embodiments relate to a photoacoustic sensor. More specifically, embodiments relate to a photoacoustic sensor with adaptive operating frequency.

BACKGROUND

Potentially hazardous atmospheres are found in many locations. These hazardous atmospheres exist due to the presence of toxic gases, combustible gas mixtures or the excess or deficiency of oxygen.

Many types of gas detection instruments have been developed to provide a warning that the atmosphere contains potentially hazardous components, or to initiate remedial action. Examples of these gas detection instruments include the detection of combustible gases in coal mines, hydrogen sulfide in oil fields and water treatment plants, carbon monoxide in places ranging from steel mills to bedrooms, and oxygen in confined spaces, such as sewers.

The reliability of toxic gas detectors is of great importance in many applications, especially when these instruments are used for ensuring the safety of personnel. Reliability is typically obtained by periodic checking of the instrument response to a test gas, however calibration test gases are typically supplied in large, bulky and expensive gas cylinders.

Some existing gas detection instruments include one or more gas sensors, whose function is to provide an electrical signal, which varies in response to the gas concentration. The output from many types of sensors can vary over time and sensors can fail to operate without warning.

Most gas sensors provide a relative output signal, such that the output signal is not an absolute measure of gas concentration, but merely proportional to the gas concentration. In such cases, the gas sensor must be calibrated with a known test gas prior to use.

Calibration may also be required as a function check to ensure the sensor is working. Calibrating a gas sensor can often times be time consuming, expensive and cumbersome in many applications.

Some conventional sensors may suffer from unpredictable baseline drift and span drift. If the sensor is not sensitive or fast enough, unacceptable undetected toxic analyte events or high False Alarm Rates (FAR) may occur.

Photoacoustic sensors may be used to detect sample gases based on the tendency of molecules of sample gases to reach higher relative levels of molecular vibration and rotation when the sample gases are exposed to certain frequencies of radiant energy. These higher relative levels of molecular vibration and rotation cause the sample gases to reach a higher temperature and pressure.

When the amplitude of the radiant energy is modulated, the resulting fluctuations in energy available for absorption produce corresponding temperature and pressure fluctuations. A sensitive detector can be used to generate electrical output signals that represent the pressure fluctuations of the sample gases.

These corresponding electrical output signals can be analyzed to evaluate properties or attributes of the sample gases. However, conventional photoacoustic sensors have a sensitivity to environmental acoustic noise sources, especially when the environmental acoustic noise sources exist at the sensors operating frequency.

One of the drawbacks with existing photoacoustic sensors is that since each environment has a unique noise content, most existing photoacoustic sensors are not typically able to readily separate the acoustic noise from the desired relevant photo acoustic signal by filtering. Therefore, a need exists for a photoacoustic sensor that minimizes acoustic noise interference when analyzing electrical output signals to evaluate properties or attributes of sample gases.

BRIEF DESCRIPTION OF THE DRAWINGS

Some embodiments are illustrated by way of examples, and not by way of limitations, in the figures of the accompanying drawings in which.

DETAILED DESCRIPTION

Figure 1:
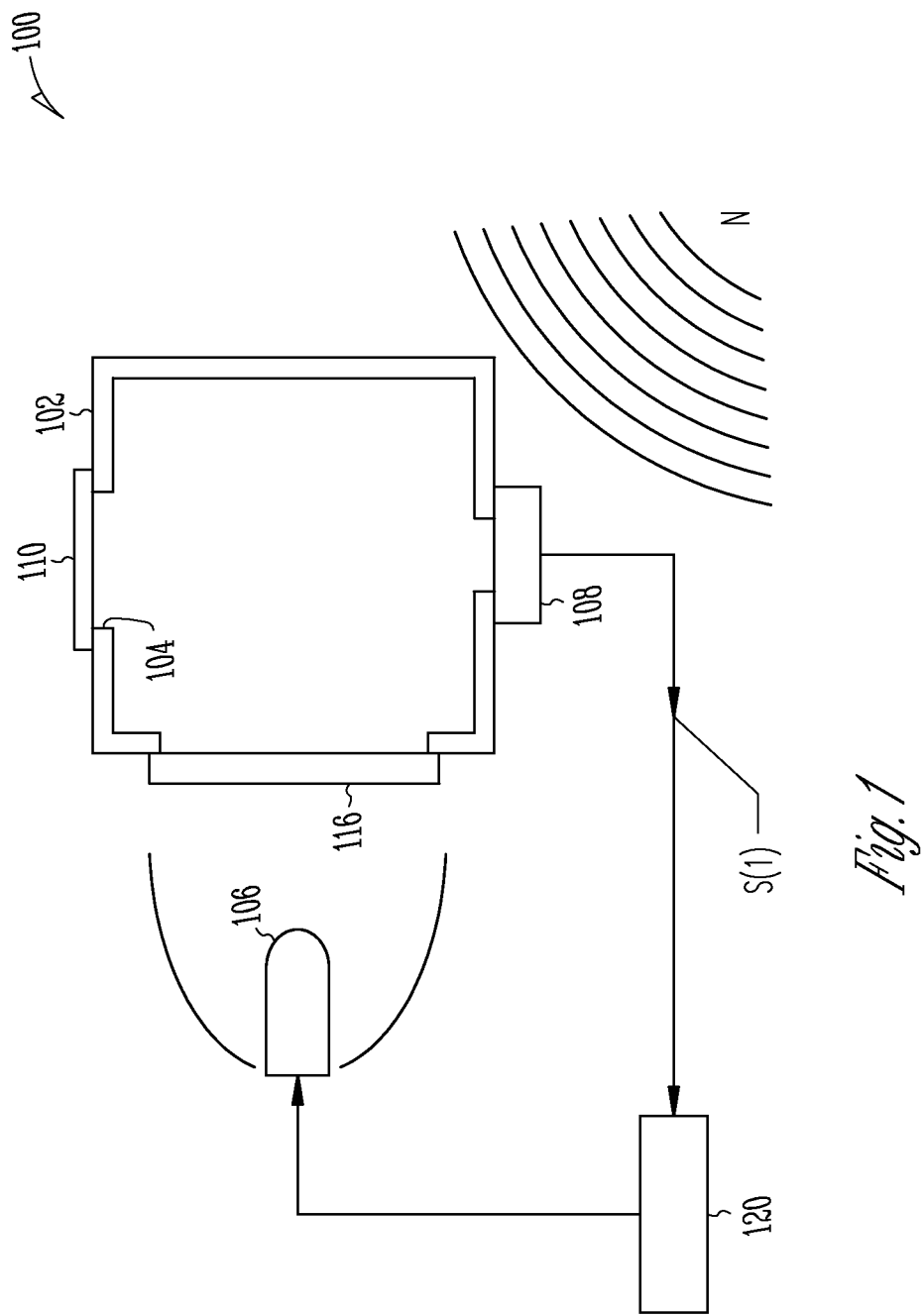
FIG. 1 is a diagram illustrating a photoacoustic sensor according to an example embodiment where the photoacoustic sensor is collecting pressure fluctuations within a gas cell to determine a spectral content of pressure fluctuations generated by noise within an ambient environment on a sample gas with the gas cell.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation.

Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Various embodiments described herein utilize photoacoustic gas detection to detect and identify gas samples. One principle of photoacoustic gas detection is based on the measurement of the pressure variation generated in a gas cell or chamber by selective absorption of infrared radiation by the target gas.

A measurement includes sampling periods and detecting periods. During detecting, the sample gas in the gas cell may be irradiated with, for example, a modulated narrow-band infrared radiation. The sample gas then heats and cools as incident infrared radiation is modulated.

These temperature fluctuations in turn generate pressure waves, which are detected by a detector (e.g., a microphone). The microphone generates an electrical output signal, which can be processed and analyzed to identify substances existing in the sample gas and evaluate the properties or attributes, for example the concentration values, of the sample gas collected in the gas cell.

Various embodiments of the application provide a photoacoustic sensor, which includes: a gas cell or chamber having an opening; a light source to generate a radiation to radiate sample gas within the gas cell; a detector to detect the sample gas within the gas cell to generate output electrical signals in response to acoustic signals generated by pressure fluctuations of the radiated sample gas caused by the radiation; and a membrane that is aligned with the opening of the gas cell. The membrane permits the sample gas to enter the gas cell.

The detector collects pressure fluctuations within the ambient environment (i.e., noise) when the light source is not producing radiation to determine spectral content of the pressure fluctuations within the ambient environment. A control receives signals from the detector that represent the spectral content of the pressure fluctuations within the ambient environment. The control adjusts a frequency of the radiation produced by the light source to a frequency that conflicts less with the spectral content of the pressure fluctuations within the ambient environment.

By measuring the acoustic noise signature with the microphone while the IR source inactive, a sensor operating frequency can be selected that minimizes acoustic noise interference. The acoustic noise signature can be measured by adjusting the reference frequency used by the lock-in with the IR source disabled. The operating frequency can be chosen that minimizes the noise content.

In some embodiments, the membrane is replaced with an active valve having a speaker aligned with the opening of the gas cell. The speaker may have a similar or identical structure to a loudspeaker. For example, the speaker may have a permanent magnet, a voice coil, and a diaphragm (or cone) attached to the voice coil. The speaker can be used to control the access of the gas cell by applying a control signal, which can be either an AC control signal or a DC control signal.

Figure 2:
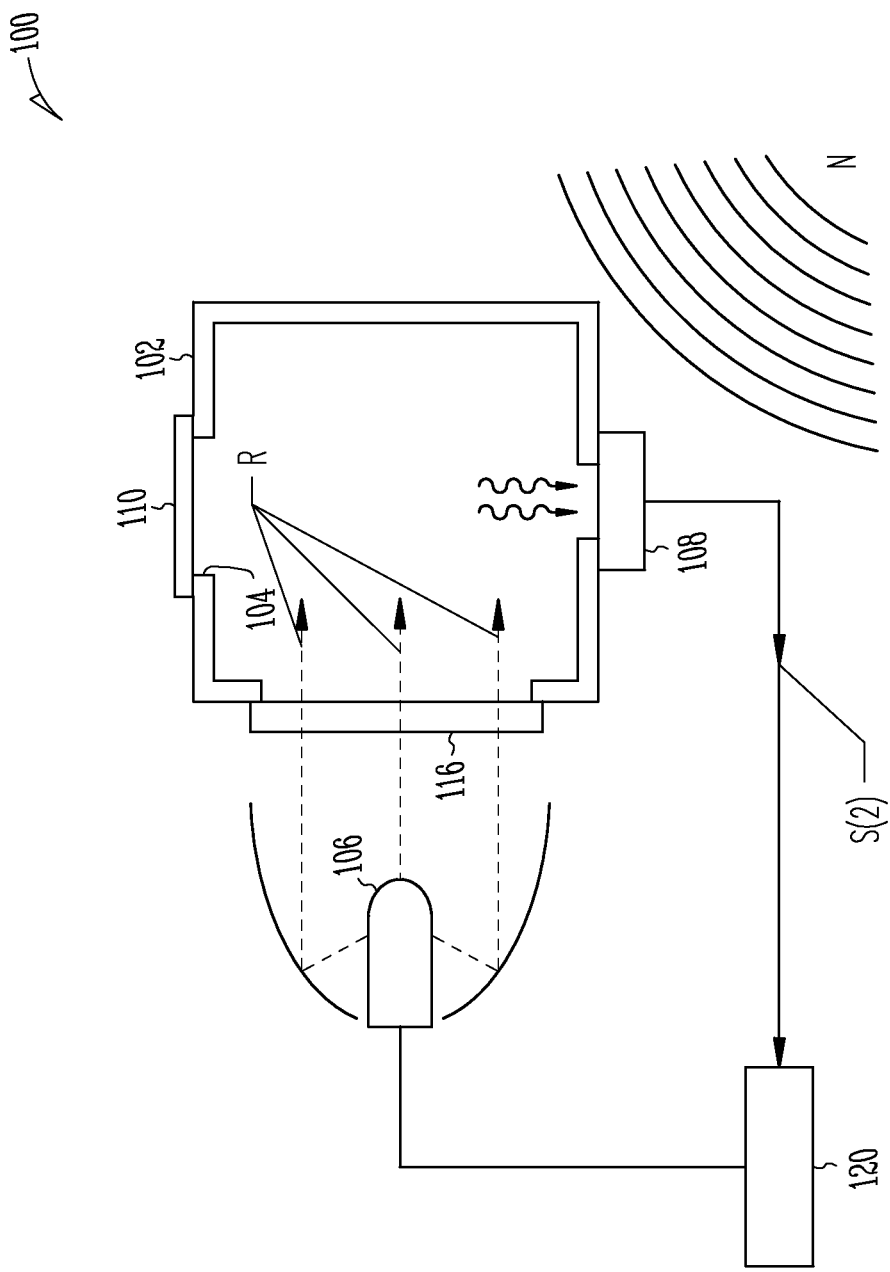
FIG. 2 shows the photoacoustic sensor of FIG. 1 where the photoacoustic sensor is collecting pressure fluctuations within a gas cell to determine a spectral content of the pressure fluctuations of a radiated gas with the gas cell.

FIGS. 1 and 2 are block diagrams of a photoacoustic sensor 100 according to an example embodiment. The photoacoustic sensor 100 may comprise: a gas cell 102 with an opening 104; a light source 106 to generate a radiation to radiate sample gas within the gas cell 102; a detector 108 to detect the sample gas within the gas cell 102; and membrane 110 aligned with the opening 104 of the gas cell 102 to permit sample gas to enter gas cell 102. The detector 108 collects pressure fluctuations within the ambient environment (i.e., noise) when the light source 106 is not producing radiation to determine spectral content of the pressure fluctuations of the noise N within the ambient environment.

As shown in FIG. 1, a control 120 receives signals S1 from the detector 108 that represent the spectral content of the pressure fluctuations due to noise N within the ambient environment. As shown in FIG. 2, the control 120 adjusts a frequency of the radiation R produced by the light source 106 to a frequency that conflicts less with the spectral content of the pressure fluctuations due to noise N within the ambient environment. The detector 108 generates output electrical signals S2 in response to acoustic signals generated by pressure fluctuations of the radiated sample gas.

The detector 108 may be for example a microphone, which may generate electrical output signals OS in response to acoustic signals generated by pressure fluctuations of the radiated sample gas caused by the radiation from the light source 106. In one embodiment, the microphone 108 is provided access to pressure variations in the sample gas, yet provides a seal to prevent gas from entering or escaping from gas cell 102 other than by the opening 104.

In some embodiments, the photoacoustic sensor 100 may further comprise a light filter 116 (or filters), which is positioned between the light source 106 and the gas cell 102 to filter the radiation into the gas cell. In some embodiments, a modulator may be used to modulate the radiation R generated by the light source 106 during detecting the sample gas. In one embodiment, the light filter 116 also provides a seal to prevent gas from entering or escaping from gas cell 102 other than by the opening 104.

As an example, during detecting, an infrared light source 106 may be modulated to radiate the sample gas in the gas cell 102 to cause the sample gas within the gas cell 102 to heat and cool as incident infrared radiation R is modulated. These temperature fluctuations in turn generate pressure waves, which may be detected by the microphone 108, and thus generate an electrical output signal OS. The electrical output signal OS from the microphone 108 can be processed and analyzed to evaluate the properties or attributes of the sample gas sealed in the gas cell 102.

As an example, by analyzing an obtained spectrum of the sample gas sealed in the gas cell 102, users may identify substances existing in the sample gas, and determine the concentration of the substances in the sample gas within the gas cell 102. Various known techniques may be used to detect the properties or attributes of the sample gas by using the photoacoustic sensor of the present application. It should be noted that embodiments are contemplated where the spectral content of the ambient noise is collected and/or analyzed simultaneously with the spectral content that is generated by the pressure waves produced by the radiated sample.

Other example embodiments relate to a method that includes providing a sample gas to an opening of a gas cell and determining a spectral content of the pressure fluctuations within the ambient environment. The method further includes supplying data to a control that spectral content of the pressure fluctuations within the ambient environment. The method further includes using the control to direct a light source to emit radiation at a frequency that minimizes conflicting pressure fluctuations with the spectral content of the pressure fluctuations within the ambient environment and generating an output signal representative of pressure fluctuations of the radiated gas sample.

Figure 3:
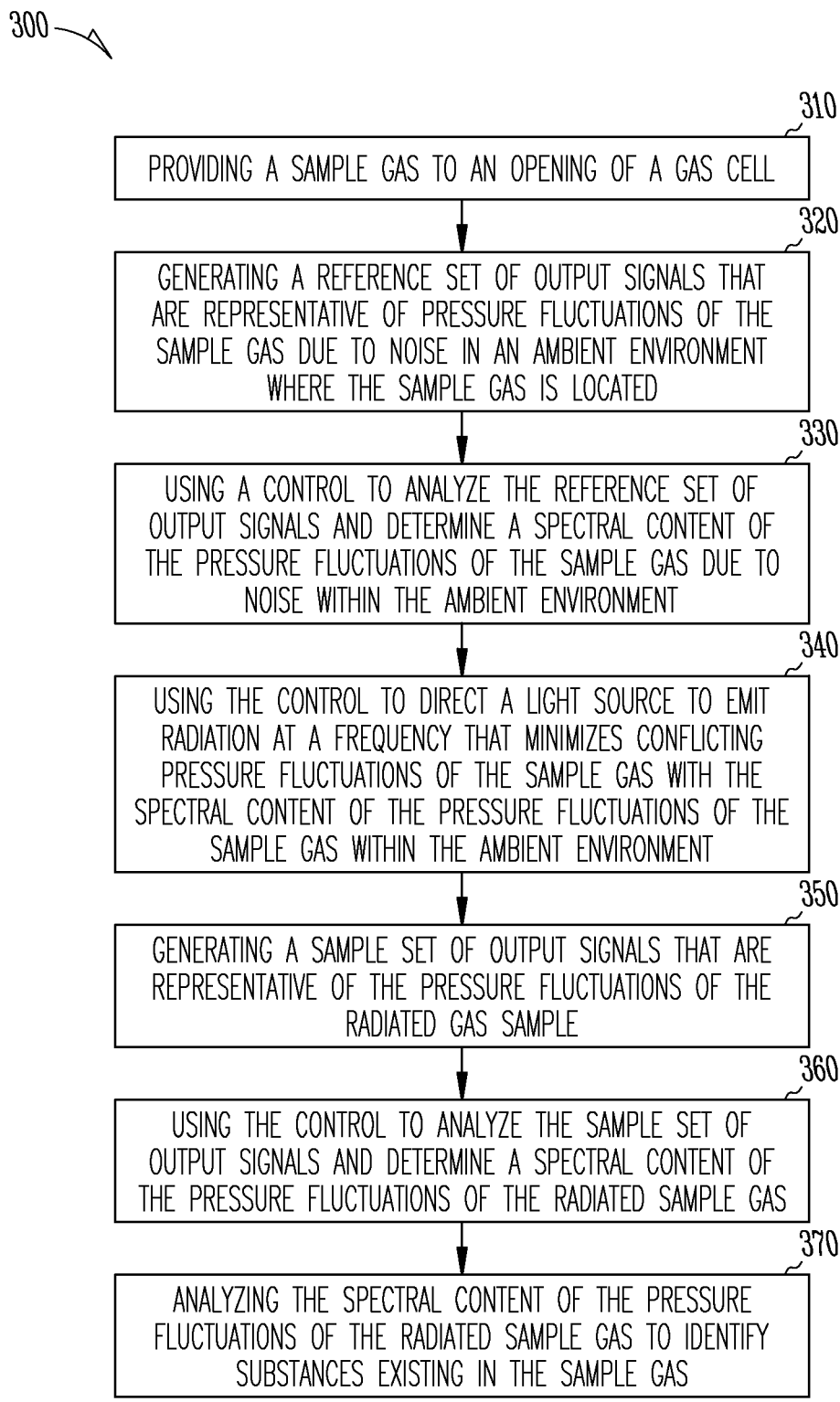
FIG. 3 is a flow diagram illustrating a method identifying substances existing in a sample gas.

Another example method 300 is shown in FIG. 3. The method 300 includes [310] providing a sample gas to an opening of a gas cell, and [320] generating a reference set of output signals that are representative of pressure fluctuations of the sample gas due to noise in an ambient environment where the sample gas is located.

The method 300 further includes [330] using a control to analyze the reference set of output signals and determine a spectral content of the pressure fluctuations of the sample gas due to noise within the ambient environment, and [340] using the control to direct a light source to emit radiation at a frequency that minimizes conflicting pressure fluctuations of the sample gas with the spectral content of the pressure fluctuations of the sample gas within the ambient environment.

The method 300 further includes [350] generating a sample set of output signals that are representative of the pressure fluctuations of the radiated gas sample, and [360] using the control to analyze the sample set of output signals and determine a spectral content of the pressure fluctuations of the radiated sample gas.

In some embodiments, [310] providing a sample gas to an opening of a gas cell includes passing the sample gas through a membrane. In other embodiments, [310] providing a sample gas to an opening of a gas cell includes activating a speaker to expose the opening in the gas cell.

It should be noted that [320] generating a reference set of output signals that are representative of pressure fluctuations of the sample gas due to noise in an ambient environment where the sample gas is located may include detecting the pressure fluctuations with a microphone. In addition, [350] generating an output signal representative of pressure fluctuations of the radiated gas sample may includes detecting the pressure fluctuations of the radiated gas sample with a microphone.

The method may further include filtering the radiation after the light source emits the radiation and before radiation reaches the sample. In addition, [360] using the control to direct a light source to emit radiation may include using the light source to emit modulated narrow-band infrared radiation.

The method may further include [370] analyzing the spectral content of the pressure fluctuations of the radiated sample gas to identify substances existing in the sample gas. In some embodiments, [370] analyzing the spectral content of the pressure fluctuations of the radiated sample gas to identify substances existing in the sample gas may include determining the concentrations of the substances existing in the sample gas.

While there has been described herein the principles of the application, it is to be understood by those skilled in the art that this description is made only by way of example and not as a limitation to the scope of the application. Accordingly, it is intended by the appended claims, to cover all modifications of the application which fall within the true spirit and scope of the application.

The invention claimed is:

1. A photoacoustic sensor comprising:
a gas cell having an opening;
a light source to generate radiation to radiate sample gas within the gas cell;
a detector to collect pressure fluctuations within the gas cell when the light source is not producing radiation to determine a spectral content of the pressure fluctuations within the ambient environment; and
a control that receives signals from the detector that represent the spectral content of the pressure fluctuations within the ambient environment, the control adjusting a frequency of the radiation produced by the light source to a frequency that conflicts less with the spectral content of the pressure fluctuations within the ambient environment, wherein the detector generates output electrical signals in response to acoustic signals generated by pressure fluctuations of the radiated sample gas.

2. The photoacoustic sensor of claim 1, further comprising a light filter positioned between the light source and the gas cell to filter the radiation radiated into the gas cell.

3. The photoacoustic sensor of claim 2, wherein the light filter provides a seal to prevent gas from entering the gas cell other than by the opening.

4. The photoacoustic sensor of claim 1, wherein the detector is a microphone.

5. The photoacoustic sensor of claim 4, wherein the microphone engages the pressure variations in the sample gas and provides a seal to prevent the sample gas from entering the gas cell other than by the opening.

6. The photoacoustic sensor of claim 1, further comprising a membrane that is aligned with the opening of the gas cell to permit the sample gas to enter the gas cell.

7. The photoacoustic sensor of claim 1, further comprising a speaker that is activated to expose the opening of the gas cell to permit the sample gas to enter the gas cell.

8. The photoacoustic sensor of claim 1, wherein the light source emits modulated narrow-band infrared radiation.

9. The photoacoustic sensor of claim 1, wherein the control operates the photoacoustic sensor to alternate between a sampling period where a sample gas enters the gas cell and a detecting period where the light source radiates the sample gas within the gas cell.

10. A method comprising:
providing a sample gas to an opening of a gas cell;
generating a reference set of output signals that are representative of pressure fluctuations of the sample gas due to noise in an ambient environment where the sample gas is located;
using a control to analyze the reference set of output signals and determine a spectral content of the pressure fluctuations of the sample gas due to noise within the ambient environment;
using the control to direct a light source to emit radiation at a frequency that minimizes conflicting pressure fluctuations of the sample gas with the spectral content of the pressure fluctuations of the sample gas within the ambient environment;
generating a sample set of output signals that are representative of the pressure fluctuations of the radiated gas sample; and
using the control to analyze the sample set of output signals and determine a spectral content of the pressure fluctuations of the radiated sample gas.

11. The method of claim 10, wherein providing a sample gas to an opening of a gas cell includes passing the sample gas through a membrane.

12. The method of claim 10, wherein providing a sample gas to an opening of a gas cell includes activating a speaker to expose the opening in the gas cell.

13. The method of claim 10, wherein generating a reference set of output signals that are representative of pressure fluctuations of the sample gas due to noise in an ambient environment where the sample gas is located includes detecting the pressure fluctuations with a microphone.

14. The method of claim 10, generating an output signal representative of pressure fluctuations of the radiated gas sample includes detecting the pressure fluctuations of the radiated gas sample with a microphone.

15. The method of claim 10, further comprising filtering the radiation after the light source emits the radiation and before radiation reaches the sample.

16. The method of claim 10, wherein using the control to direct a light source to emit radiation includes using the light source to emit modulated narrow-band infrared radiation.

17. The method of claim 10, further comprising analyzing the spectral content of the pressure fluctuations of the radiated sample gas to identify substances existing in the sample gas.

18. The method of claim 10, wherein analyzing the spectral content of the pressure fluctuations of the radiated sample gas to identify substances existing in the sample gas includes determining the concentrations of the substances existing in the sample gas.

19. A photoacoustic sensor comprising:
a gas cell having an opening;
a membrane that is aligned with the opening of the gas cell to permit the sample gas to enter the gas cell;
a light source to generate radiation to radiate sample gas within the gas cell;
a light filter positioned between the light source and the gas cell to filter the radiation radiated into the gas cell, wherein the light filter provides a seal to prevent gas from entering the gas cell other than by the opening;
a microphone to detect the sample gas within the gas cell, wherein the microphone generates output electrical signals in response to acoustic signals generated by pressure fluctuations of the radiated sample gas caused by the radiation, and wherein the microphone collects pressure fluctuations within the ambient environment when the light source is not producing radiation to determine spectral content of the pressure fluctuations within the ambient environment; and
a control that receives signals from the microphone that represent the spectral content of the pressure fluctuations within the ambient environment, the control adjusting a frequency of the radiation produced by the light source to a frequency that conflicts less with the spectral content of the pressure fluctuations within the ambient environment, wherein the control operates the photoacoustic sensor between an alternating sampling period where a sample gas enters the gas cell and a detecting period where the light source radiates the sample gas within the gas cell.

20. The photoacoustic sensor of claim 19, wherein the light source emits modulated narrow-band infrared radiation.

* * * * *